(12) United States Patent
Ruers et al.

(10) Patent No.: US 11,937,909 B2
(45) Date of Patent: Mar. 26, 2024

(54) MAGNETIC MARKER, LOCATION DETECTION SYSTEM, INTRODUCER AND METHOD

(71) Applicants: Stichting Het Nederlands Kanker Instituut-Antoni Van Leeuwenhoek Ziekenhuis, Amsterdam (NL); Universiteit Twente, Enschede (NL)

(72) Inventors: Theodoor Jacques Marie Ruers, Amsterdam (NL); Bram Schermers, Amsterdam (NL); Bennie Ten Haken, Amsterdam (NL)

(73) Assignee: Sirius Medical Systems B.V., Eindhoven (NL)

( * ) Notice: Subject to any disclaimer, the term of this patent is extended or adjusted under 35 U.S.C. 154(b) by 0 days.

(21) Appl. No.: 15/521,918

(22) PCT Filed: Oct. 27, 2015

(86) PCT No.: PCT/NL2015/050745
§ 371 (c)(1),
(2) Date: Apr. 26, 2017

(87) PCT Pub. No.: WO2016/068700
PCT Pub. Date: May 6, 2016

(65) Prior Publication Data
US 2017/0319101 A1    Nov. 9, 2017

(30) Foreign Application Priority Data

Oct. 27, 2014    (NL) ..................................... 2013686

(51) Int. Cl.
*A61B 5/06*    (2006.01)
*A61B 5/05*    (2021.01)
(Continued)

(52) U.S. Cl.
CPC ................ *A61B 5/062* (2013.01); *A61B 5/05* (2013.01); *A61B 10/02* (2013.01); *A61B 90/39* (2016.02);
(Continued)

(58) Field of Classification Search
CPC ........... A61B 5/062; A61B 90/39; A61B 5/05; A61B 10/02; A61B 2090/3908;
(Continued)

(56) References Cited

U.S. PATENT DOCUMENTS

2003/0052785 A1*  3/2003  Gisselberg ........... A61B 5/6883
                                                         340/572.8
2004/0236169 A1    11/2004  Slater et al.
(Continued)

FOREIGN PATENT DOCUMENTS

EP    1 413 251 A1    4/2004
WO    01/08578 A1     2/2001
(Continued)

OTHER PUBLICATIONS

Wapler et al. "Magnetic properties of materials for MR engineering, micro-MR and beyond", Journal of Magnetic Resonance. Apr. 2014. p. 1-18 (Year: 2014).*

*Primary Examiner* — Keith M Raymond
*Assistant Examiner* — Sean A Frith
(74) *Attorney, Agent, or Firm* — Hoffmann & Baron, LLP (57) ABSTRACT

A magnetic marker for use in locating tissue for surgery includes a casing and two to five magnetic elements arranged in a row. The two or more magnetic elements are separated from each other by an isolating material. The magnetic marker may be non-bio-absorbable. This means that the magnetic marker is invariable as it does not decay over time. This invariability ensures that on the basis of the signal measured by a magnetometer device a distance
(Continued)

between a probe of the magnetometer device and the magnetic marker can be determined.

12 Claims, 7 Drawing Sheets

(51) Int. Cl.
    *A61B 10/02*     (2006.01)
    *A61B 90/00*     (2016.01)
    *A61M 37/00*     (2006.01)
    *G01N 27/72*     (2006.01)
    *G01R 33/02*     (2006.01)

(52) U.S. Cl.
    CPC ......... *A61M 37/0069* (2013.01); *G01N 27/72* (2013.01); *G01R 33/02* (2013.01); *A61B 2090/3908* (2016.02); *A61B 2090/3954* (2016.02); *A61B 2090/3987* (2016.02)

(58) Field of Classification Search
    CPC ... A61B 2090/3954; A61B 2090/3987; A61M 37/0069; G01N 27/72; G01R 33/02
    See application file for complete search history.

(56) References Cited

U.S. PATENT DOCUMENTS

| | | | | |
|---|---|---|---|---|
| 2008/0033286 A1* | 2/2008 | Whitmore | ............. | A61B 90/39 600/426 |
| 2009/0131734 A1* | 5/2009 | Neustadter | ........... | A61N 5/1049 600/8 |
| 2009/0306728 A1* | 12/2009 | Wright | ................. | A61B 5/4041 607/45 |
| 2010/0036241 A1* | 2/2010 | Mayse | ................... | A61B 1/018 600/435 |
| 2010/0049033 A1* | 2/2010 | Kawano | ................... | A61B 5/06 600/117 |
| 2011/0137154 A1 | 6/2011 | Hattersley et al. | | |
| 2012/0189551 A1* | 7/2012 | Frank | ..................... | A61K 49/10 424/9.36 |
| 2015/0008914 A1* | 1/2015 | Hartwig | ................. | G01N 27/72 324/252 |

FOREIGN PATENT DOCUMENTS

| | | | | |
|---|---|---|---|---|
| WO | WO-0108578 A1 * | 2/2001 | ............ | A61B 90/39 |
| WO | 2011/067576 A1 | 6/2011 | | |
| WO | WO-2013114247 A2 * | 8/2013 | ............ | A61B 19/54 |
| WO | 2014/013235 A1 | 1/2014 | | |

* cited by examiner

MAGNETIC MARKER, LOCATION DETECTION SYSTEM, INTRODUCER AND METHOD

CROSS-REFERENCE TO RELATED APPLICATIONS

This application is the National Stage of International Application No. PCT/NL2015/050745 filed Oct. 27, 2015, which claims the benefit of Netherlands Application No. NL 2013686, filed Oct. 27, 2014, the contents of which is incorporated by reference herein.

FIELD OF THE INVENTION

The present invention relates to a magnetic marker, a system to arrange a magnetic marker at a place of interest, and a method of preparing tissue of interest in a patient for excision by surgery.

Breast cancer is the most common form of cancer in women and is associated with high mortality figures. Improved diagnostic procedures and intensified screening have increased the incidence of small, non-palpable breast lesions over the past decades. Concurrently, the preferred treatment shifted from radical mastectomy to Breast Conserving Surgery (bcs). In BCS of non-palpable lesions, localisation technologies such as Wire-Guided Localisation (wgl), Radioactive Occult Lesion Localisation (roll) and Radioactive Seed Localisation (rsl) are indispensable.

Although literature shows ample benefit of both radioactive technologies over the antiquated wire-guided approach, clinical adoption is only as low as 25% in Dutch hospitals, and presumably lower in other countries. This means that at least 75% of women is still treated using WGL, an unnecessarily painful, logistically challenging and highly inaccurate technology. In a reported 20% to 50% of cases a reoperation is necessary which is highly unfavorable. The primary reason for this low clinical adoption of radioactive techniques is the laborious nature of implementing radioactive techniques due to strict regulations, as well as the limited accessibility of medical radioisotopes. The European committee writes that the global demand for radioisotopes is met by only five nuclear production reactors, which range in age from 42 to 51 years. The Nuclear Energy Agency (NEA) further estimates that the demand for medical isotopes will already exceed supply in 2015. Therefore, there is a clear demand for non-isotope based alternatives to radioactive health-care solutions.

The present application relates to a novel technique analogous to RSL, but based upon the physical principle of magnetism, rather than radioactivity.

WO2014/013235 A1 discloses a magnetic marker for surgical localization for use in non-palpable breast cancer. The magnetic marker of WO2014/013235 A1 comprises magnetic nanoparticles and a bio-absorbable matrix.

According to the disclosure of WO2014/013235 A1, the bio-absorbable magnetic marker is placed at a biopsy site directly after a biopsy sample has been removed from the tissue of interest. When thereafter the pathology analysis indicates that the tissue of interest should be removed from the patient, the tissue for surgery may be located by using a magnetic detection probe configured to detect the magnetic marker.

In case the pathology analysis indicates that no tissue has to be removed from the patient, the magnetic marker remains in the body of the patient and the magnetic marker will be absorbed over the course of time.

Although an advantage of the procedure of WO2014/013235 A1 is that the magnetic marker will be placed directly after the biopsy sample has been removed from the body of the patient, a drawback of this method is that, when the pathology analysis indicates that no tissue of interest should be removed from the patient, the magnetic marker has already been introduced into the body of the patient, while it will not be used to locate the tissue for surgery. This means that a foreign body is brought into the tissue of a patient without it being used. This may potentially interfere with future diagnostic procedures or otherwise may induce unwanted side effects, which is generally undesirable.

Further, the magnetic marker may be present in the body of the patient for a long time, in particular when the pathology analysis indicates that no tissue of interest should be removed from the patient. It may take a considerable long time before the magnetic marker of WO2014/013235 A1 is absorbed by the body in which it is placed.

It is remarked that it is, generally, also undesirable to perform surgery only to remove the magnetic marker out of the patient.

BACKGROUND OF THE INVENTION

The present invention provides an alternative magnetic marker for use in locating tissue for surgery, wherein the magnetic marker comprises a casing and a multiple, preferably two to five, magnetic elements arranged in a row in the casing.

The magnetic elements of the invention are bodies of ferromagnetic material having a predetermined size and shape. The magnetic elements are unmagnetized, but have a high magnetic susceptibility. This means that the magnetic elements show a relatively large magnetization in the presence of an externally applied magnetic field.

The use of the magnetic marker of the invention is based on the insight that the magnetic marker is only introduced into the patient after it has been determined that tissue has to be removed from the patient.

As the magnetic marker will only be placed in tissue to be removed from the patient, the magnetic marker may be optimized for detectability of the magnetic marker with a magnetometer device within the patient and introduction of the magnetic marker into the patient. The magnetic marker does not have to be bio-absorbable, since the magnetic marker will always be removed from the patient during future surgery.

The detectability of the magnetic marker may be increased by arranging a relatively large amount of magnetic material in the magnetic marker. However, an increased amount of magnetic material may lead to an increased volume of magnetic material in the magnetic marker, and thus larger dimensions of the magnetic marker.

Increased dimensions of the magnetic marker also increase the size of the area that will be localized by a magnetic detection technique detecting the position of the magnetic marker of the invention. Since a goal of the localization technique may be to obtain a signal hotspot at or nearby the tumour location, i.e. the tissue to be removed, it is undesirable that the dimensions of the hotspot are relatively large. Therefore, the dimensions of the magnetic marker should not be unnecessarily large. The maximum dimension of the magnetic marker is for example less than 15 mm, preferably in the range of 3 to 10 mm.

Further, it is desirable that the introduction of the magnetic marker into the patient does not involve a large impact on the body of the patient. An advantageous way of introducing the magnetic marker into the patient and bring it to the desired location is using an introducer in the form of or comprising a hollow needle. Such an introducer may for example be a hollow needle with dimensions comparable to conventional biopsy needles, or hypodermic needles.

The magnetic marker may be accommodated in the hollow needle and dispensed from this needle, after that the distal needle end has been positioned in the desired location for implantation of the magnetic marker.

In order to accommodate a magnetic marker with a maximum of magnetic material in the hollow needle, the magnetic marker preferably comprises an elongated shape, preferably an elongated cylindrical shape with a circular cross section.

However, when a single elongated magnetic element, such as a relatively long piece of wire, is held within the range of a magnetometer device, the measurement signal obtained by the magnetometer device when moving its probe in axial direction over the wire will have two peaks. Each of these peaks is associated with moving past one of the opposite ends of the wire. In the area between the two peaks the measurement signal received by the magnetometer device may be substantially lower than the signal of the two peaks.

The peaks and the substantially lower measurement signal in the middle segment of the wire is caused by the anisotropic shape of the wire. When the length of the wire element is increased the peaks will also move away from each other, leaving a larger area with a lower measurement signal between the peaks. When the wire element is shortened, the peaks will move towards each other. When the wire element is sufficiently short, the two peaks will jointly form a single peak. In that case the anisotropic effect described above is no longer detected by the magnetometer device.

Figure 1:
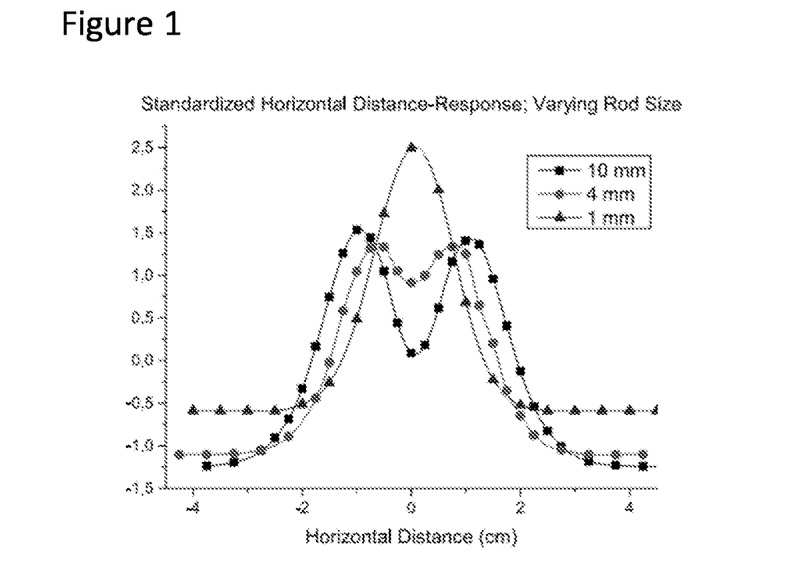
FIG. 1 shows the anisotropic effect of different wire lengths on the measurement signal obtained by a magnetometer device moved in axial direction along the respective wires.

FIG. 1 shows the measurement signal obtained by a Sentimag magnetometer device moved over three different lengths of wire, in axial direction thereof. The wire lengths are 10, 4 and 1 mm long and arranged at the origin (0,0). The wires are made of STS UNS S42000 and each have a diameter of 1 mm.

In FIG. 1, it can be seen that the 10 mm and 4 mm wires clearly shows two peaks and the substantially lower measurement signal in the middle segment, whereby the difference between the peaks and the middle part is substantially smaller for the 4 mm wire compared with the 10 mm wire. The measurement signal of the 1 mm wire does not show two peaks, but only one peak directly above the wire. The magnetometer device does not detect an anisotropic effect with the wire of 1 mm.

Figure 2:
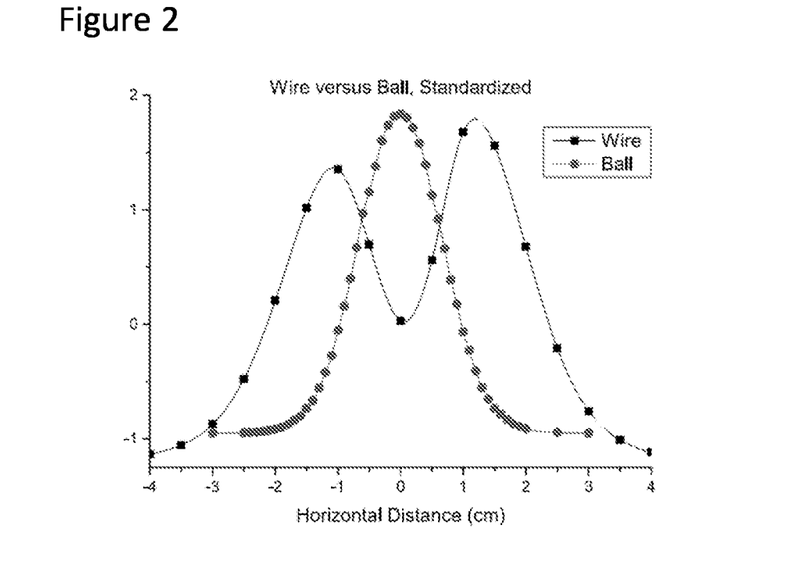
FIG. 2 shows the measurement signal obtained by a magnetometer device moved in axial direction along an anisotropic wire element versus the measurement signal obtained by a magnetometer device moved in axial direction along an isotropic spherical element.

FIG. 2 shows the difference between the measurement signal obtained by a magnetometer device moved in axial direction along an anisotropic wire element versus the measurement signal obtained by a magnetometer device moved in axial direction along an isotropic spherical element.

It is concluded that in order to improve the detectability of the magnetic marker, it is advantageous to use magnetic elements having a relatively short length, relative to its diameter, such that an anisotropic effect is not detected by the magnetometer device.

For example, when using cylindrical magnetic elements, the length and the diameter of the magnetic element may be about the same, for example within a deviation range of maximally 20%, preferably maximally 10%.

In another embodiment, the magnetic elements may each have isotropic shapes, such as spheres or balls, to avoid the anisotropic effect.

The magnetic marker of the invention comprises multiple magnetic elements arranged in a row. By providing multiple magnetic elements arranged in a row, whereby the anisotropic effect for each of the magnetic elements is eliminated or at least substantially reduced with respect to the magnetometer device used, or not present, an elongated magnetic marker having a high detectability is provided as a large volume of magnetic material may be arranged within an elongated magnetic marker.

This arrangement of a plurality of magnetic elements in a row provides an elongated shape of the magnetic marker that is suitable to be introduced into the patient, for example using a hollow needle.

Preferably, the two or more magnetic elements are spaced with respect to each other. By preventing direct physical contact between the two or more magnetic elements, the chance that the two or more magnetic elements magnetically act as a single element, and therewith creating a anisotropic shape, is substantially reduced.

In an embodiment, the two or more magnetic elements are separated by an isolating material. To avoid that the two or more magnetic elements magnetically act as a single element, magnetically isolating material may be arranged between each two adjacent magnetic elements. This isolating material may be provided in the form of films or other layers of isolating material, such as a teflon film, which is arranged between the magnetic elements.

In an alternative embodiment, each magnetic element may be completely coated and/or encapsulated with the isolating material. In yet another embodiment, the casing may be formed by isolating material and encapsulate each of the magnetic elements such that the magnetic elements are isolated with respect to each other.

An isolating material is a material that has a low or negative magnetic susceptibility. This means that the isolating material shows a relatively low magnetization in the presence of an externally applied magnetic field.

Materials that may be used as isolating materials are polyimide film, such as Kapton film (http://www.dupont-.com/products-and-services/membranes-films/polyimide-films/brands/kapton-polyimide-film.html) or fluoroplastic films and sheets, for example fluorinated ethylene propylene (FEP) or Perfluoroalkoxy (PFA) films and sheets, such as Teflon film (https://www.chemours.com/Teflon_Industrial/en_US/products/product_by_type/films/index.html)

In an embodiment, the magnetic marker is non-bio-absorbable, for example by providing a casing of non-bio-absorbable material or by providing a non-bio-absorbable coating over the casing.

By providing a non-bio-absorbable magnetic marker, the magnetic marker is made invariable over time. In other words, the magnetic marker does not decay over time. The advantage of such magnetic marker is that the magnetic characteristics will also remain the same in the course of time.

The advantage of an invariable, in particular non-bio-absorbable, magnetic marker is that the magnitude of the measurement signal, for example a number of counts per time period, received by the magnetometer device can be used to determine a distance between the probe of the magnetometer device and the magnetic marker.

The magnetometer device may be calibrated for typical tissue such that the magnitude of the measurement signal received by the magnetometer device can be directly related to an associated distance. It has been found that with the magnetic marker according to the invention, the distance between a probe and the magnetic marker can be determined within a distance measurement range of about 0 to 5 cm with an accuracy of about 2 mm. This answers a clear clinical need during surgery.

The determination of the distance between the probe and the magnetic marker is very useful for a surgeon during detection and removal of tissue to be removed from the patient because it will give him more guidance about the location of the tumor leading to more precise tumor surgery.

It is remarked that in the method of WO2014/013235 A1 the magnetic material is only detected in a crude way, without the possibility to measure the distance from the detection probe to the material, a feature which is very relevant in order to perform more precise surgery and remove all tumor tissue while sparing as much normal tissue as possible.

In an embodiment, the two or more magnetic elements each have a largest dimension, and wherein the largest dimension, for example the diameter or length of the respective magnetic element, may be in the range of 1.1 to 2.3 mm, preferably between 1.2 and 1.7 mm, more preferably 1.2, 1.3, 1.4, 1.5. 1.6 or 1.7 mm.

The dimension of each of the two or more magnetic elements in a direction perpendicular to the direction of the largest dimension is preferably in the same range.

It has been found that a row of magnetic elements having a largest dimension in the range of 1.1 to 2.3, in particular 1.2 to 1.7 mm, have sufficient magnetic material to enable proper detection of the magnetic marker within a measurement range of 3 to 4 cm, while at the same time the magnetic marker may be designed with a relatively small transverse dimension. Such distance measurement range of 3 to 4 cm is useful in many applications, in particular in the detection of the magnetic marker in a breast.

In an embodiment, the two or more magnetic elements have the same shape. It is advantageous to use multiple magnetic elements each having the same shape, such as wire, plug, rod, ball, of material or beads, spheres, balls or particles. In an embodiment, the two or more magnetic elements may have a cylindrical or spherical shape, such as wire, rod or balls, wherein the magnetic elements each have the same diameter and/or length.

To provide a magnetic marker having a high detectability, it is desirable that a substantial part of the volume of the magnetic marker is filled with magnetic elements. In an embodiment the magnetic marker comprises a cylindrical shape having a diameter, wherein a diameter of the magnetic elements is 0.5-0.99 times the diameter of the cylindrical shape.

In an embodiment, the magnetic marker has a cylindrical shape having a diameter between 0.5 and 2.4 mm, preferably between 0.8 mm and 2.0 mm, and a length less than 15 mm, preferably between 3 and 10 mm, more preferably between 3 and 5 mm.

A magnetic marker having these dimensions is suitable to be received by a hollow needle. Suitable conventional hollow needles may for example be 12 G, 14 G, 16 G, 18 G (gauge) needles having an inner diameter of 0.8 to 2.4 mm. A pusher element may be provided in the hollow needle to push the magnetic marker out of the needle, as soon as the needle end has been positioned at the desired location.

Further, the maximum dimensions of the magnetic marker are sufficiently short to enable the surgeon to detect with the magnetometer device a relatively delimited part of tissue to be removed.

At the same time, the length and width of the magnetic marker provide sufficient volume to house magnetic elements that allow to determine a position of the magnetic marker with respect to a probe of the magnetic detection device within a distance range of for example 0 to 4 cm.

In an embodiment, the casing comprises an annular sleeve, wherein the two or more magnetic elements are solid cylindrical elements arranged next to each other in the casing, and one or more isolating layers are arranged between the two or more magnetic elements. The casing may further comprise two cover plates to cover the opposite open ends of the sleeve.

Such an embodiment allows a relatively simple construction to create a magnetic marker according to the invention. To produce the magnetic marker, the two or more cylindrical magnetic elements may be arranged in the annular sleeve with the isolating layer arranged between the two magnetic elements. The inner diameter of the sleeve substantially corresponds with the outer diameter of the cylindrical magnetic elements.

The cover plates are provided and connected to the sleeve to completely occlude the open ends of the sleeve such that the cover plates and sleeve form a closed casing around the magnetic elements. In one embodiment, the cover plates are arranged on the open ends of the sleeve after the magnetic elements and the one or more isolating layers are arranged in the sleeve. In another embodiment, one of the cover plates may be an integral part of the sleeve, while the other cover plate is fixed to the open end of the sleeve once the magnetic elements and the one or more isolating layers are arranged via this open end in the sleeve.

In yet another embodiment, the sleeve is formed and closed around the magnetic elements and one or more isolating layers in one procedure, thus forming a closed sleeve with integral cover plates.

In an alternative embodiment of the magnetic marker, the magnetic elements are spherical magnetic elements arranged in a casing that surrounds and/or encapsulates the magnetic elements.

The magnetic elements of a magnetic marker according to the invention comprise a ferromagnetic material. This magnetic material may, for example, be a metal, such as cobalt, iron, or nickel, a metal alloy, rare earth and transition metal alloy, M-type or spinel ferrite containing aluminium, barium, bismuth, cerium, chromium, cobalt, copper, dysprosium, erbium, europium, gadolinium, holmium, iron, lanthanum, lutetium, manganese, molybdenum, neodymium, nickel, niobium, palladium, platinum, praseodymium, promethium, samarium, strontium, terbium, thulium, titanium, vanadium, ytterbium, and yttrium, or a mixture thereof.

The magnetic elements may also be formed by metglas or Mu-metal.

The magnetic elements can also be formed by oxidizing a combination of an iron (II) salt and another metal salt. The metal salts which are beneficial include salts of aluminum, barium, bismuth, cerium, chromium, cobalt, copper, dysprosium, erbium, europium, gadolinium, holmium, iron, lanthanum, lutetium, manganese, molybdenum, neodymium, nickel, niobium, palladium, platinum, praseodymium, promethium, samarium, strontium, terbium, thulium, titanium, vanadium, ytterbium, and yttrium.

Preferably, the magnetic elements are made from other ferromagnetic materials including soft iron, ferrites, stainless steels, nickel and related composites. Most preferably the magnetic elements are made of Stainless steel (STS), Ferritic STS, Martensitic STS and Duplex STS.

The casing is preferably a bio-compatible casing. The biocompatible casing may be made of biocompatible material and/or comprise a biocompatible coating.

The casing is preferably also a non-bioabsorbable casing.

Suitable forms and shapes of the casing are clips, springs, coils, wires, cylinders, rings, annular shapes and elements formed from sheet material.

The invention further provides a system to locate tissue for surgery, comprising:
- a magnetic marker as described herein, and
- a magnetometer device configured to detect the location of the magnetic marker, wherein the magnetometer device comprises a probe, and wherein the magnetometer device is preferably configured to determine a distance between the probe and the magnetic marker.

A magnetometer device is configured to determine a magnitude of a magnetic field. The magnetometer device may comprise a magnetometer as disclosed in US2011137154 A1 and WO2011067576 A1. Such a magnetometer is brought on the market as SentiMag magnetometer by Endomagnetics Ltd. UK, (http://www.endomagnetics.com/sentimag).

The magnetometer comprises a magnetic probe to detect the magnetic marker and a signal readout device to process the measurement signal, for example to show the magnitude of the measurement signal on a display device.

The magnetometer device may further comprise a processing device to process the measurement signal. The processing device may be part of the magnetometer itself or a separate device such as a computer.

The processing device may be configured to determine a distance between the probe and the magnetic marker on the basis of a magnitude of the measurement signal of the magnetometer. The relationship between the magnitude of the measurement signal and the associated distance between the probe and the magnetic marker may be stored in the processing device, for example in a look-up table or a mathematical relationship.

When a measurement signal is received by the magnetometer device, the processing device may determine, on the basis of the magnitude of the measurement signal and the stored relationship, an associated distance between the probe and the magnetic marker. Any other way to store and use the relationship between the magnitude of the measurement signal and the associated distance between the magnetic marker and the probe may also be used.

In order to reliably determine the distance between the probe and the magnetic marker on the basis of the magnitude of the measurement signal over a prolonged time, in particular between implantation of the magnetic marker and removal of the tissue in which the magnetic marker is arranged, it is of importance that the magnetic characteristics of the magnetic marker do not change over time. Therefore, it is preferred that the magnetic marker is non-bio-absorbable and of a defined form and size.

The method to determine the distance between the probe and the magnetic marker may be implemented as a computer program product adapted to perform the step of determining the distance between the probe and the magnetic marker on the basis of the magnitude of the measurement signal received by the magnetometer device.

This computer program product may comprise software code adapted to perform, when executed in a processing device, the steps of:
- receiving a measurement signal obtained by a probe of a magnetometer arranged at a distance from a magnetic marker and/or a magnitude of the measurement signal; and
- determining the distance between the probe and the magnetic marker on the basis of the magnitude of the measurement signal.

The step of determining the distance may comprise calculating the distance using a mathematical relationship between the distance and the magnitude of the measurement signal and/or using a look-up table comprising a relationship between the distance and the magnitude of the measurement signal.

When the processing device receives the measurement signal, the software code may also be adapted to perform the step of determining the magnitude of the measurement signal on the basis of the received measurement signal.

The invention may also provide an introducer to introduce a magnetic marker at a location of interest, comprising:
- a hollow needle, and
- one or more magnetic markers as described herein loaded or to be loaded in the hollow needle.

The introducer may comprise a conventional hollow needle. The size of such needles may vary as varies the size of biopsy needles. For example, conventional biopsy needles may be 12 G, 14 G, 16 G or 18 G (gauge) needles having an inner diameter of approximately 0.8-2.4 mm. Thus, a diameter of the magnetic marker is between 0.5 mm and 2.4 mm preferably between 0.8 mm and 2.0 mm which allow to use hollow needles for marker introduction with already clinically accepted diameters.

The length of the magnetic marker is preferably also sized to fit into a hollow needle, the length of the magnetic marker is for example maximally 15 mm, preferably in the range of 3 to 10 mm.

The introducer may comprise a pusher element that can be moved through the hollow needle to push the one or more magnetic markers out of the hollow needle. The pusher element may for example extend through the hollow needle and extend from the proximal end of the needle in order to allow the user to push the pusher element in the distal direction of the needle to push the magnetic marker, at the desired location, out of the distal end of the hollow needle.

The invention further provides a method of preparing tissue of interest in a patient for excision by surgery, comprising the steps of;
- performing an analysis of a sample of the tissue of interest;
- if the analysis indicates that the tissue of interest should be removed placing a magnetic marker as described herein at the site of interest, e.g. by a radiologist under image guidance; and
- locating the tissue for surgery by detecting the magnetic marker using a magnetometer device.

Analysis can be performed via known technologies in the art and are for example not limited to pathological analysis or imaging analysis. The sample (or tissue of interest) can be a biopsy sample and the magnetic marker can be inserted at this biopsy site or close to it.

The magnetic marker can be placed at the site of interest using an imaging technique such as mammography, ultrasound, PET, MRI or CT.

The magnetic marker is preferably inserted after the biopsy (or tissue of interest) has been analyzed and diagnosed as being a lesion that should be surgically removed. Alternatively the magnetic marker can be placed at a site of interest that is suspected to be or diagnosed to be from a cancer lesion by means of imaging for example mammography, ultrasound, PET, MRI or CT or any other imaging modality. Alternatively the tissue can be diagnosed as a lesion that should be surgically removed by means of pathological examination for example histology or cytology.

The magnetic marking and localization method described above is not limited in its application to breast cancer lesions as tissue of interest and can be applied in any indication where marking of a surgical site is needed. Other examples of suitable cancer lesions are liver or lung cancer, colorectal cancer, bowel cancer, head and neck cancer, soft tissue cancer, urologic and gynaecologic cancers, lymph node metastases of any cancer and recurrent cancers of any type and at any site in the body.

The method may further comprise the step of determining the distance between a probe of the magnetometer device and the magnetic marker. As explained above, the distance between the probe of the magnetometer device and the magnetic marker may be determined on the basis of the magnitude of the measurement signal received by the probe. In the step of locating the tissue for surgery, knowledge on the distance between the probe and the magnetic marker may be useful information for the surgeon in order to properly decide on the tissue material to be removed from the body.

BRIEF DESCRIPTION OF THE DRAWINGS

Embodiments of the invention will now be described, by way of example only, with reference to the accompanying schematic drawings in which.

DETAILED DESCRIPTION OF THE INVENTION

Figure 3:
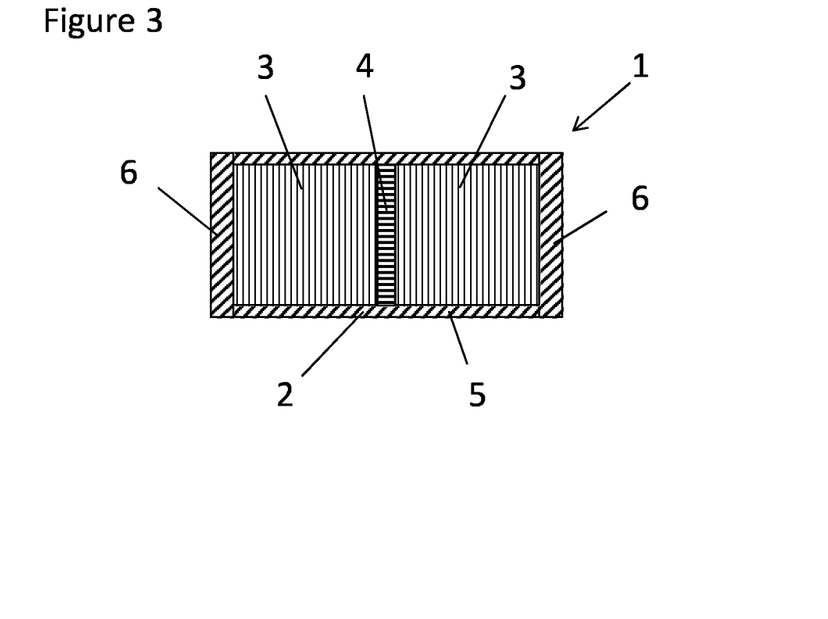
FIG. 3 depicts schematically a cross section of a first embodiment of a magnetic marker according to the invention.

FIG. 3 shows a first embodiment of a magnetic marker according to the invention, generally indicated by reference numeral 1. The magnetic marker 1 comprises a casing 2 and two magnetic elements 3 arranged within the casing 2. The magnetic elements 3 are made of magnetic stainless steel. Between the two magnetic elements 3, an isolating layer 4 is provided. The isolating layer 4 is formed by a Teflon film arranged between the two magnetic elements 3.

The casing 2 is formed by a titanium annular sleeve 5. The opposite open ends of the cylindrical sleeve 5 are each closed by a cylindrical cover plate 6. The cylindrical cover plates 6 are also formed by titanium and connected, for example by welding, gluing or bonding, to the sleeve 5 in a sealing manner to form a closed biocompatible and non-bio-absorbable casing 3. In an alternative embodiment, one cover plate may be an integral part of the sleeve.

The magnetic elements 3 have a cylindrical shape with a diameter of about 1.5 mm and a length of about 1.5 mm. The thickness of the isolating layer is 0.10 mm. The sleeve 5 has a thickness of about 0.1 mm. The diameter of the cover plates 6 is 1.7 mm and the thickness of the cover plates 6 is 0.2 mm.

This results in an overall length of the magnetic marker 1 of 3.5 mm and a diameter of 1.7 mm. With these dimensions, the magnetic marker 1 can be arranged in a 14 G hollow needle.

Figure 4:
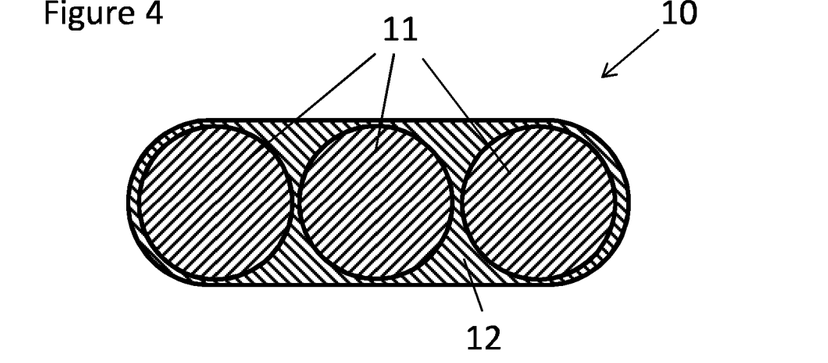
FIG. 4 depicts schematically a cross section of a second embodiment of a magnetic marker according to the invention.

FIG. 4 shows a second embodiment of a magnetic marker 10 according to the invention. The magnetic marker 10 comprises three spherical magnetic elements 11 encapsulated in a biocompatible casing 12.

In an embodiment, the diameter of the spherical magnetic elements 11 is about 1.5 mm, while the diameter of the casing is about 1.6 mm. The casing 12 has a maximum length of 4.6 mm and the radius of the rounded ends of the casing 12 is 0.8 mm.

The biocompatible casing may be made of or comprise, for example as a coating, natural or synthetic polymers including biocompatible plastic, resins, silicons, dextrans, carboxydex trans, Polyethylene glycol (PEG), Poly vinyl alcohol (PVA), polyvinylpyrrolidone (PVP), polyethyleneimine (PEI), polyglucose sorbitol carboxymethylether and chitosan. Other coating materials include metals such as gold, pegylated colloidal gold nanoparticles, silver; carbon, silica, silicones, aminosilanes, NuSil MED-4750 and ceramics.

The casing 12 may also be coated with biocompatible coating material such as dextran, carboxydextran, other sugars, albumin, PEG, or biocompatible polymers, resins or NuSil MED-4750.

The casing 12 can be any material that is surrounding or casting or encapsulating the spheres or balls.

The casing 12 may for example be in the form of a casted mold wherein the mold is filled with for example a biocompatible resin and the spherical magnetic elements 11 are enclosed within this cast. The casing 12 to be coated can for example be composed of epoxy.

Figure 5:
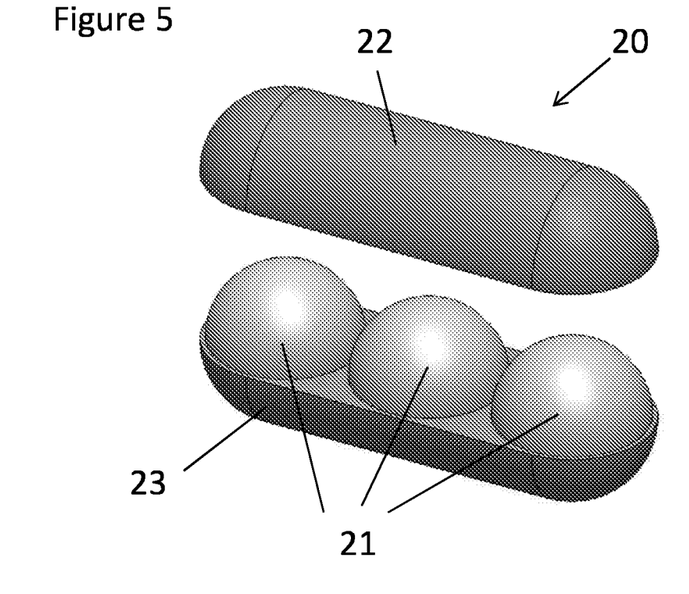
FIG. 5 depicts a third embodiment of a magnetic marker according to the invention.

FIG. 5 shows another embodiment of a magnetic marker 20 according to the invention. The magnetic marker 20 comprises three spherical magnetic elements 21 encapsulated in a biocompatible casing 22, 23.

The casing 22, 23 is composed of two halves that are configured to enclose the spherical magnetic elements 21 in a sealing manner. In FIG. 5, the casing is shown in exploded view, in which the magnetic elements 21 are arranged in the lower casing half 23 and the upper casing half is shown spaced from the magnetic elements 21.

Figure 6:
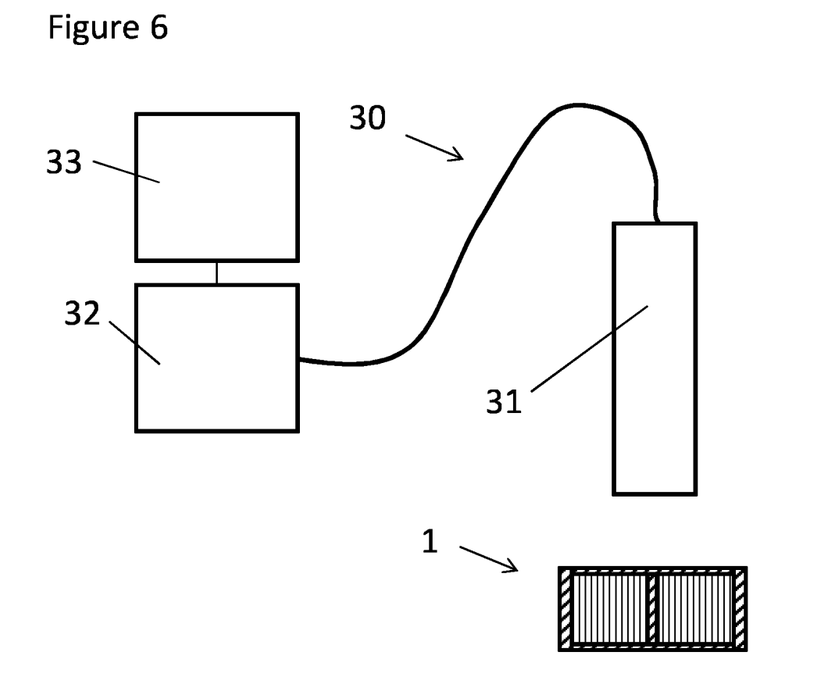
FIG. 6 depicts schematically a combination of a magnetometer device and a magnetic marker.

FIG. 6 shows schematically a magnetometer device 30 arranged to determine a location of a magnetic marker 1. The magnetometer device 30 comprises a probe 31, a read-out device 32 and a processing device 33. The read-out device 32 is coupled to the probe 31 in order to receive a measurement signal of the probe 31.

The processing device 33 is coupled to the read-out device 32 to receive measurement signals, directly or after processing, from the read-out device 32.

The processing device 33 may for example be a computer configured to combine a measurement signal received from the magnetometer with processed signals of other imaging or measurement techniques. The processing device 33 may also be arranged in the same housing as the read-out device 32. In such embodiment, the processing device 33 may be integrated in a processing device of the read-out device 32.

The processing device 33 may be configured to determine a distance between the probe 31 and the magnetic marker 1 on the basis of a magnitude of a measurement signal received by the probe 31. The method to determine the distance between the probe 31 and the magnetic marker 1 may for instance be implemented as a computer program comprising software code adapted to, when executed on the processing device 33, perform this method.

Figure 7:
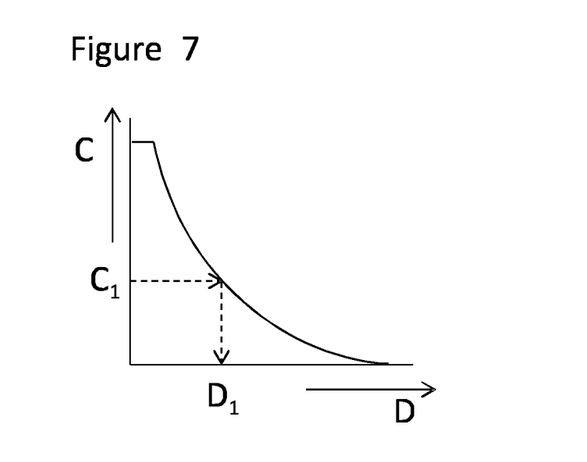
FIG. 7 depict a relationship between distance between the probe and the magnetic marker and a measurement signal value of the magnetometer device.

FIG. 7 shows a typical relationship between the magnitude of a measurement signal C received by the probe 31 and the distance D between the probe 31 and the magnetic marker 1.

When the distance D becomes smaller than a certain value, for example 3 cm, the magnetic marker 1 comes within the measurement range of the probe 31 and the probe 31 starts to detect a measurement signal. When the distance between the probe 31 and the magnetic marker 1 is made smaller, the magnitude of the measurement signal will increase until a saturated measurement signal is obtained, for example when the distance becomes smaller than for instance 0.5 cm.

It is remarked that in other embodiments for example with other settings of the magnetometer device 30, the saturated measurement signal will not be noticeably present within the distance range.

In the distance range between the larger distance where a very small measurement signal is received and the smaller distance where the maximum measurement signal for that magnetic marker 1 is received, the magnitude of the measurement signal can be used to determine the distance between the probe 31 and the magnetic marker 1.

The relationship between the magnitude of the measurement signal and the associated distance, as shown in a graph in FIG. 7, may be obtained by calibration of the combination of the magnetometer device 30 and the magnetic marker 1 and stored in the processing device 33. When a measurement signal C1 is obtained by the magnetometer device 30, the processing device 33 may then determine the associated distance D1 as shown by dashed arrows in FIG. 7.

The relationship between magnitude of measurement signal and distance may be stored in any suitable form in the processing device 33, such as a mathematical relationship or a look-up table It has been found that with the configuration of the magnetic markers 1, 10 shown in FIGS. 1 and 2 and a Sentimag magnetometer of Endomagnetics Ltd, UK, the distance between the probe 31 and the magnetic marker 1 can be determined within a distance range of 0 to 4 cm, in particular 1 to 3.5 cm with an accuracy of about 2 mm.

Such accuracy provides the surgeon important guidance in localization of the tissue of interest using the magnetic markers 1, 10.

There may be a considerable time period between the placement of the magnetic marker 1 and the surgery for removal of the tissue in which the magnetic marker 1 is placed. In order to be able to accurately measure, after such time period, the distance between the probe 31 and the magnetic marker 1, it is desirable that the magnetic properties of the magnetic marker 1 have not changed during this time period. To avoid change in the magnetic properties, the magnetic marker is non-bio-absorbable, for example by providing a casing of non-bio-absorbable material or by providing a non-bio-absorbable coating on the casing.

Figure 8:
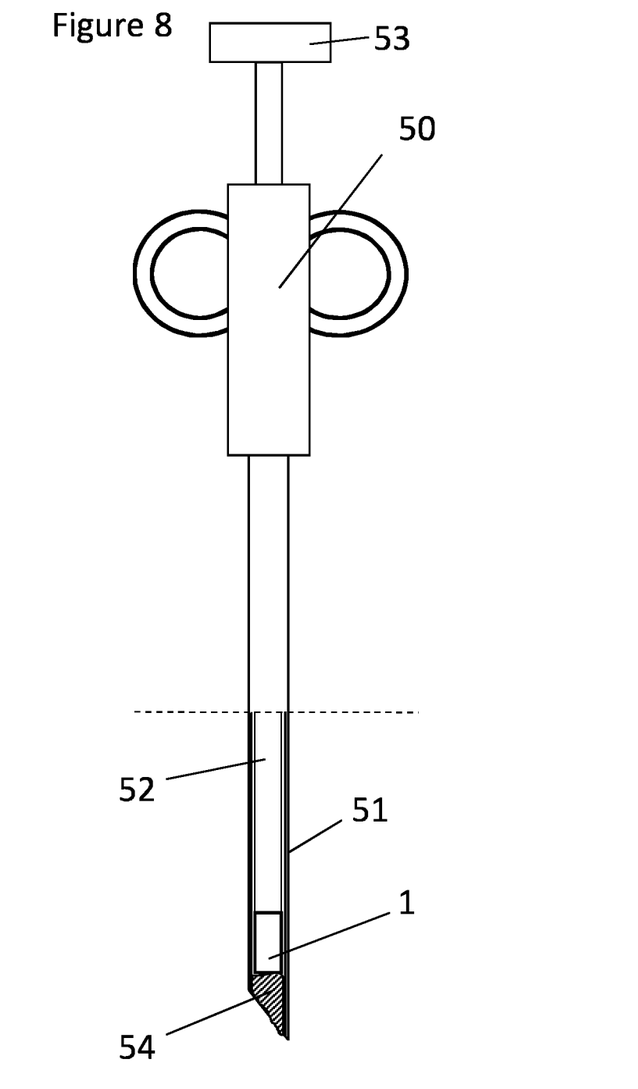
FIG. 8 depicts an introducer for magnetic markers loaded with a magnetic marker.

FIG. 8 shows an introducer 50 loaded with a magnetic marker 1. The needle comprises a hollow outer needle 51, a solid inner sleeve 52 that fits within outer needle 51 with a handle 53 at the proximal end for manual handling of the inner sleeve 52.

At the distal end of the hollow needle 51 a quantity of bone wax is provided to prevent premature release of the magnetic marker 1 from the needle.

When the distal end of the needle 51 loaded with the magnetic marker 1 is brought at a desired location, the inner sleeve 52 can be used as a pusher element to push by means of handle 53 the magnetic marker 1 out of the needle 51.

The needle 51 is a 14 G needle with an inner diameter of approximately 1.7 mm. As can be seen in FIG. 8, the elongated magnetic marker 1 having an outer diameter of 1.7 mm fits properly in the hollow outer needle 51.

In order to efficiently carry out a step of arranging the magnetic marker 1 at a desired location, the introducer 50 may be provided preloaded with one or more magnetic markers 1, for example in a sterile package. Or alternatively, the introducer 50 may be provided unloaded in a sterile package, and the magnetic marker 1 will be provided separately as well for manual loading.

The magnetic marker 1, 10, 20 may be used in a method of preparing tissue of interest in a patient for excision by surgery. The method comprises the step of performing an analysis of a sample of the tissue of interest. The sample of the tissue of interest may for example be obtained by taking a biopsy sample of the tissue of interest. The biopsy sample may be analyzed and diagnosed as being of a cancer lesion. If the analysis indicates that the tissue of interest should be removed a magnetic marker 1, 10, 20 may be placed at the site of interest.

FIGS. 9a-9d show an ex-vivo proof of principle of the use of the magnetic marker 20 in human breast tissue.

Figure 9A:
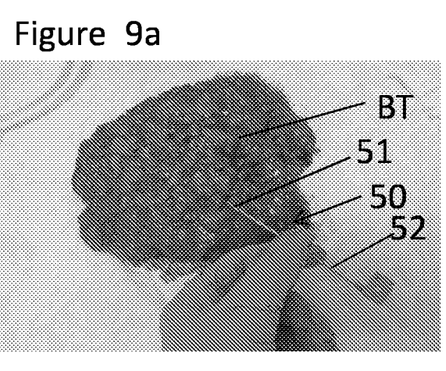
FIGS. 9a-9d show images of the use of the magnetic marker in human breast tissue.

FIG. 9a shows the step of placing the magnetic marker 10 in breast tissue BT at a desired location. The magnetic marker 10 can be placed at the site of interest using an imaging technique such as mammography, ultrasound, PET, MRI or CT or any imaging technology. To place the magnetic marker 10 at the desired location using an introducer 50 having a needle 51 and a pusher element 52.

Figure 9B:
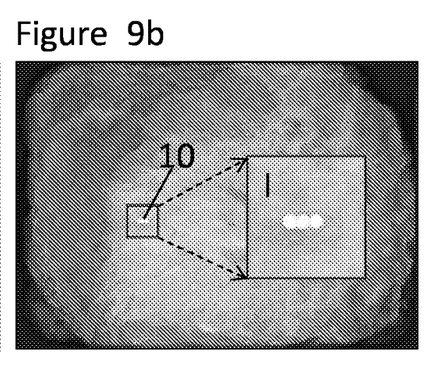

FIG. 9b shows on a mammography imaging the magnetic marker 10 arranged in the breast tissue. In the insert I, a magnified view of the magnetic marker is shown.

Figure 9C:
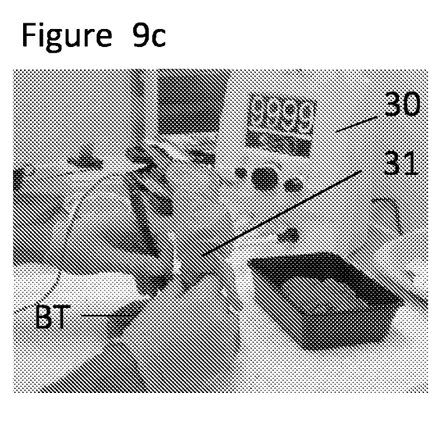

FIG. 9c shows the use of the magnetometer device 30, wherein the probe 31 is arranged on the breast tissue to locate the position of the magnetic marker 10 within the breast tissue BT. During localization of the magnetic marker 10, resection of the magnetic marker 10 and surrounding tissue is started using bipolar tweezers. On the basis of the localization of the magnetic marker 10, a lump of breast tissue is excised from the breast tissue BT. During actual use of the magnetic marker 10 in practice, this lump of breast tissue is the tissue to be removed from the body of the patient.

Figure 9D:
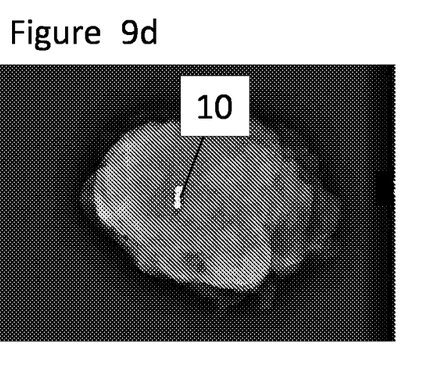

FIG. 9d shows a mammography of the excised lump of breast tissue which was made to confirm that the magnetic marker 10 is present in the excised tissue.

It has been shown that the magnetic marker 10 can be successfully used to remove tissue of interest from a body of a patient.

The magnetic marker 1, 10, 20 can be used in combination with several imaging techniques, and the location of the magnetic marker 1, 10, 20 can be determined using this technique.

Figure 10A:
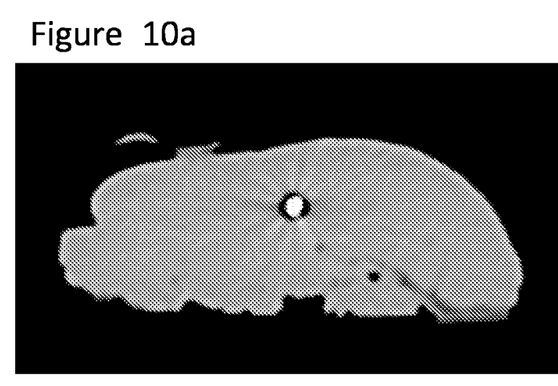
FIGS. 10a-10c show images obtained by different imaging techniques of a chicken breast in which a magnetic marker has been introduced.
Figure 10B:
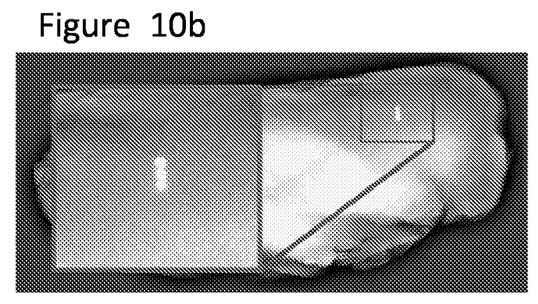
Figure 10C:
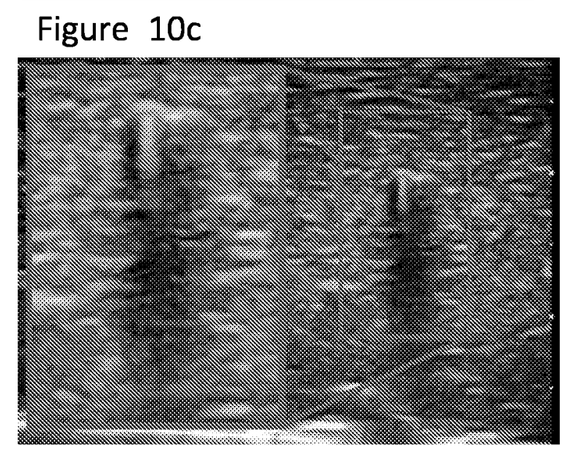

FIG. 10a-c show images obtained by different imaging techniques of a chicken breast in which a magnetic marker 10 has been introduced.

FIG. 10a shows an image of the chicken breast obtained by a CT scanning device; FIG. 10b shows an mammography image of the chicken breast; and FIG. 10c shows an image obtained by an ultrasound device.

The invention claimed is:

1. A magnetic marker for use in locating tissue for surgery, comprising:
   a casing, wherein the casing comprises an annular sleeve having a constant outer diameter, and
   two or more magnetic elements arranged in a row in the casing, wherein the two or more magnetic elements are solid cylindrical elements arranged in the sleeve,
   wherein the two or more magnetic elements are made of ferromagnetic material, and
   wherein a flat film of magnetically isolating material is provided between two adjacent magnetic elements,
   wherein the two or more magnetic elements are separated by the film of magnetically isolating material, and
   wherein the magnetic marker is non-bio-absorbable.

2. The magnetic marker of claim 1, wherein the two or more magnetic elements each have a largest dimension, and wherein the largest dimension is between 1.2 and 1.7 mm.

3. The magnetic marker of claim 1, wherein the two or more magnetic elements have a largest dimension, wherein the largest dimension of the magnetic elements is in the range of 0.1-0.99 times a largest dimension of the casing.

4. The magnetic marker of claim 1, wherein the two or more magnetic elements have the same shape.

5. The magnetic marker of claim 1, wherein the magnetic marker comprises a cylindrical shape having a diameter, and wherein a diameter of the magnetic elements is 0.5-0.99 times the diameter of the cylindrical shape.

6. The magnetic marker of claim 1, wherein the magnetic marker has a cylindrical shape having a diameter between 0.5 and 2.4 mm.

7. The magnetic marker of claim 1, wherein the magnetic marker has a cylindrical shape having a diameter between 0.8 mm and 2.0 mm, and a length between 3 and 10 mm.

8. The magnetic marker of claim 1, wherein the casing and the film of isolating material are made of different materials.

9. A system to locate tissue for surgery, comprising:
   a magnetic marker as claimed in claim 1, and
   a magnetometer device configured to detect the location of the magnetic marker,
   wherein the magnetometer device comprises a probe, and
   wherein the magnetometer device is configured to determine a distance between the probe and the magnetic marker.

10. An introducer to introduce a magnetic marker at a location of interest, comprising:
    a hollow needle, and
    one or more magnetic markers as claimed in claim 1 loaded or to be loaded in the hollow needle,
    wherein the introducer comprises a pusher element that can be moved through the hollow needle to push the one or more magnetic markers out of the hollow needle.

11. A method of preparing tissue of interest in a patient for excision by surgery comprising the steps of;
    performing an analysis of a sample of the tissue of interest; and
    if the analysis indicates that the tissue of interest should be removed placing a magnetic marker as claimed in claim 1 at the site of interest;
    locating the tissue for surgery by detecting the magnetic marker using a magnetometer device.

12. A magnetic marker for use in locating tissue for surgery, comprising:
    a casing,
    at least two magnetic elements arranged in a row in the casing, wherein the two or more magnetic elements are made of ferromagnetic material,
    one or more isolating layers arranged between the two adjacent magnetic elements to prevent that the at least two magnetic elements magnetically act as a single element,
    wherein the casing and the one or more isolating layers are made of different materials, and
    wherein the magnetic marker is non-bio-absorbable,
    wherein the casing comprises an annular sleeve and two cover plates to cover the opposite open ends of the annular sleeve, and
    wherein the at least two magnetic elements are solid cylindrical elements arranged next to each other in the annular sleeve.

* * * * *